United States Patent [19]

Jupe et al.

[11] 4,308,112

[45] Dec. 29, 1981

[54] PROCESS FOR THE ISOLATION OF PYROCATECHOL AND HYDROQUINONE

[75] Inventors: Christoph Jupe; Jürgen Baumert, both of Cologne; Günter Schümmer, Stommeln, all of Fed. Rep. of Germany

[73] Assignee: Bayer Aktiengesellschaft, Leverkusen, Fed. Rep. of Germany

[21] Appl. No.: 166,270

[22] Filed: Jul. 2, 1980

[30] Foreign Application Priority Data

Jul. 14, 1979 [DE] Fed. Rep. of Germany ....... 2928553

[51] Int. Cl.[3] ............................................ B01D 3/10

[52] U.S. Cl. ...................................... 203/80; 203/91; 568/752; 568/753

[58] Field of Search ...................... 203/71, 73, 80, 91; 568/751, 753, 752

[56] References Cited

PUBLICATIONS

"Catalytic Hydroxylation of Phenol by Hydrogen Peroxide"; P. Maggioni et al; La Chimica E L'Industria; v 59, n 4; (Apr. 1977); pp. 239–242.

"Phenol"; Ind. Eng. Chem.; Prod. Res. Dev.; vol. 15; No. 3; (1956); pp. 212–215.

*Primary Examiner*—Frank Sever

*Attorney, Agent, or Firm*—Sprung, Felfe, Horn, Lynch & Kramer

[57] ABSTRACT

A process is described for the isolation of pyrocatechol and hydroquinone from mixtures containing the same, and phenol and higher boiling accompanying substances. The mixture can be one obtained by reacting phenol with a peroxidic hydroxylating agent and removing some of the phenol and the substances which have a lower boiling point than phenol. The mixture is subjected to a first rectification in which phenol and substances which have a boiling point between phenol and pyrocatechol are obtained overhead to leave behind a bottom product containing pyrocatechol and hydroquinone. The bottom product is subjected to a second rectification in which the pyrocatechol is obtained overhead to leave behind a bottom product containing hydroquinone and higher boiling accompanying substances. This bottom product is fed to a concentrating unit in which hydroquinone is evaporated overhead to leave behind high boiling accompanying substances as residue.

13 Claims, No Drawings

PROCESS FOR THE ISOLATION OF PYROCATECHOL AND HYDROQUINONE

The present invention relates to a process for the isolation of pyrocatechol and hydroquinone from mixtures which contain phenol, pyrocatechol, hydroquinone, high-boiling concomitant substances and, if appropriate, substances which have boiling points between those of phenol and pyrocatechol.

Pyrocatechol and hydroquinone are industrially important fine organic chemicals which are used both directly, for example in photographic developers, and as intermediate products for, for example, dyestuffs, polymerisation inhibitors, pharmaceuticals and agents for protecting plants (see Kirk-Othmer, Encyclopaedia of Chemical Technology, Second Edition, Volume 11, pages 462 to 492, in particular pages 469 and 488 (1966)).

The search for an economical and simple preparation process led, inter alia, to a number of processes for the oxidation of phenol, which give pyrocatechol and hydroquinone as co-products (see, for example, DE-OS (German Published Specification) 2,658,943, DE-OS (German Published Specification) 2,410,742, DE-OS (German Published Specification) 2,364,181, DE-OS (German Published (German Published Specification) 2,658,545, DE-OS Specification) 2,332,747, DE-OS (German Published Specification) 1,593,968, DE-OS (German Published Specification) 2,633,302, DE-AS (German Published Specification) 2,064,497, DE-OS (German Published Specification) 2,150,657, DE-OS (German Published Specification) 2,167,040, DE-OS (German Published Specification) 2,341,743, DE-OS (German Published Specification) 2,407,398, DE-OS (German Published Specification) 1,543,953 and DE-AS (German Published Specification) 2,404,114).

Relatively large amounts of pyrocatechol and hydroquinone are at present produced by these processes, as can be seen from the publications by Jean Varagnat, Ind. Eng. Chem., Prod. Res. Dev., Volume 15, No. 3, pages 212–215 (1976) and by P. Maggioni and F. Mimisci, La Chimica e l'Industria, Volume 59, No. 4, pages 239–242 (1977).

In all these processes, which are based on the hydroxylation of phenol with peroxidic reagents, an excess of phenol is necessary to achieve high selectivities. Thus, for example, the process according to DE-OS (German Published Specification) 2,407,398 requires a molar ratio of phenol to hydrogen peroxide of more than 2:1 and preferably a ratio between 10 and 3:1. At most between 10 and 50% of the phenol are thus reacted, and about 90 to 50% of the phenol employed are accordingly present as unreacted phenol after the reaction. The process according to DE-OS (German Published Specification) 2,064,497 is also preferably carried out at a molar ratio of phenol to hydrogen peroxide of 7:1 or more, so that a phenol conversion of at most 15% results and 85% of the phenol employed are accordingly still present as unchanged phenol after the reaction.

In order to be able to carry out these processes economically on an industrial scale, the unreacted phenol must thus be recovered and re-employed in the reaction. In the said processes carried out industrially, the phenol is recovered by multi-stage distillation. Since it is in general not possible to use pyrocatechol and hydroquinone together, it is also necessary to separate the pyrocatechol and hydroquinone, which is likewise in general effected by rectification.

The abovementioned publication by J. Varagnat describes the separation of the reaction mixture from the reaction of phenol, by distillation in a sequence of five rectification columns. Phenol and other auxiliary and concomitant substances are obtained as the top products in four columns and are re-used, whilst pyrocatechol and hydroquinone are separated in a fifth column and the hydroquinone is then subjected to recrystallization. In this process, high-boiling substances are separated off as the bottom product in the third and fifth column. Separating off the high-boiling substances in the third column, in which only high-boiling substances are present in the bottom product, requires complete evaporation of all of the reaction products to be isolated and of the remainder of the unreacted phenol. Since a certain amount of liquid reflux is necessary to operate the column and forms a product stream to be evaporated again, more energy, in total, must be consumed for the evaporation in the third stage than is required for a single evaporation of the vaporizable products fed in. For this—in some cases repeated—evaporation, an appropriate amount of energy must be applied, which has the effect of exposing the products to heat, since a bottom temperature of 230° C. is given for the evaporator of the third column. From the plan on page 214 of the publication by J. Varagnat, it can be seen that, in spite of the fact that the high-boiling substances have already been separated off in the third column, the quality of the bottom product of the fifth column (hydroquinone) is not suitable for the take-off. The bottom product of the fifth column is in fact recycled into the third column and hydroquinone is taken off from the fifth column as a side stream in the form of a vapour and is passed to a stage in which it is crystallized from water. High-boiling substances are thus not removed from the bottom of the third column to an extent sufficient to enable hydroquinone to be taken off as the bottom product of the fifth column.

The reaction mixture is also worked up by distillation in the process described by P. Maggioni and F. Minisci (see above). After stepwise evaporation in three separate evaporators connected in series, in each case under a lower pressure down to 13 mbars, the remaining separation of the mixture is carried out in two rectification columns. Phenol for recycling is obtained in the first column, and the products pyrocatechol and hydroquinone are obtained in the second column. In this process, the high-boiling substances are separated off as the bottom product of the third evaporator, which is operated at 13 mbars. Maintaining such a low pressure requires not inconsiderable technical effort. In this process also, not only residual phenol but also the entire amount of pyrocatechol and hydroquinone must be evaporated in order to separate off the high-boiling substances, which gives rise to consumption of energy and exposure of the product to heat. Hydroquinone is separated off from the bottom product of the last column and is then recrystallized from water. The removal of high-boiling substances from the evaporator is inadequate in this case also, since the hydroquinone must be separated off from the bottom product of the last column and then recrystallized.

A process has now been found for the isolation of pyrocatechol and hydroquinone from mixtures which contain phenol, pryocatechol, hydroquinone, high-boiling concomitant substances and, if appropriate, substances with boiling points between those of phenol and pyrocatechol, which is characterized in that (a) such mixtures are fed to a first rectification column in which the phenol and any substances present which have boiling points between those of phenol and pyrocatechol are obtained as the top product, (b) the bottom product of the first rectification column is fed to a second rectification column in which the pyrocatechol is obtained as the top product and (c) the bottom product from the second rectification column is fed to a concentrating unit in which hydroquinone is fed to a concentrating unit in which hydroquinone is evaporated and from which high-boiling concomitant substances are removed as the residue, together with small amounts of hydroquinone.

Mixtures of various compositions which contain phenol, pyrocatechol,, hydroquinone, high-boiling concomitant substances and, if appropriate, substances with boiling points between those of phenol and pyrocatechol can be employed in the process according to the invention. Suitable mixtures can be obtained, for example, when phenol is reacted with a peroxidic hydroxylating agent, if appropriate in the presence of water and/or organic solvents, and the constituents with boiling points lower than that of phenol and, if appropriate, together with these substances some of the phenol, are separated off from the reaction mixtures obtained. High-boiling accompanying substances, that is to say constituents of the mixture which have boiling points high than that of hydroquinone or which cannot be distilled without decomposition can have been formed in the hydroxylation reaction and/or in the subsequent working up stages. Substances which have boiling points between those of phenol and pyrocatechol can be high-boiling solvents employed in the hydroxylation reaction and/or by-products formed in the hydroxylation reaction or the subsequent working up stages. The mixtures employed in the process according to the invention preferably contain no substances with boiling points between those of phenol and pyrocatechol.

Mixtures which are particularly suitable for use in the process according to the invention are those which are obtained in the reaction of phenol with aqueous hydrogen peroxide or with a solution of hydrogen peroxide or a percarboxylic acid in an organic solvent with a boiling point lower than that of phenol, after the solvent and, if appropriate, the carboxylic acid corresponding to the percarboxylic acid and some of the phenol employed in excess have been removed.

For example, mixtures which contain 10 to 85% by weight of phenol, 5 to 45% by weight each of pyrocatechol and hydroquinone and 0.5 to 10% by weight of high-boiling accompanying substances can be employed in the process according to the invention. Mixtures which contain 40 to 60% by weight of phenol, 10 to 30% by weight each of pyrocatechol and hydroquinone and 1 to 10% by weight of high-boiling accompanying substances are particularly preferably employed.

In the process according to the invention, the first rectification column is operated such that all of the phenol present in the feed mixture, if appropriate together with substances with boiling points between those of phenol and pyrocatechol, passes off over the top. After condensation, some of the top product is introduced into the column, in liquid form, as the reflux. The portion of top product which remains after separating off the reflux can be further used as desired. It is preferably recycled into the hydroxylation reaction, if appropriate after separating off substances with boiling points between those of phenol and pyrocatechol.

The first rectification column can be operated, for example, under an overhead pressure in the range from 5 to 700 mbars. The overhead pressure is preferably in the range from 50 to 500 mbars, and particularly preferably in the range from 100 to 300 mbars. The first rectification column can contain, for example, between 15 and 25 theoretical plates and can be operated at a ratio of reflux to removal of 0.5 to 1.5. Preferably, the first rectification column contains 16 to 20 theoretical plates and is operated at a ratio of reflux to removal of 0.7 to 1.3. A mixture which contains pyrocatechol, hydroquinone and high-boiling concomitant substances is obtained at the bottom of the first rectification column.

This bottom product is introduced into the second rectification column. This column is operated such that virtually all of the pyrocatechol present is obtained as the top product. After condensation, some of the top product is introduced into the column, in the liquid form, as the reflux. The portion which remains after separating off the reflux is the pyrocatechol isolated according to the invention. This can also be removed in solid form, for example via a flaking roller.

The second rectification column can be operated, for example, under an overhead pressure in the range from 0.02 to 0.2 bar. The overhead pressure is preferably in the range from 30 to 100 mbars, and an overhead pressure of 40 to 70 mbars is very particularly preferred. The second rectification column can contain, for example, between 12 and 16 theoretical plates and can be operated at a ratio of reflux to removal of 1.8 to 2.5. Preferably, the second rectification column contains 13 to 15 theoretical plates and is operated at a ratio of reflux to removal of 2.0 to 2.2. A mixture which contains hydroquinone and high-boiling concomitant substances is obtained at the bottom of the second rectification column.

This bottom product is passed to a concentrating unit. Most of the hydroquinone present, for example over 95% by weight, is evaporated in the concentrating unit. The hydroquinone thus isolated can in many cases be used in the form in which it is obtained, if appropriate after condensation. If particular purity requirements are demanded, it can additionally be purified, for example by customary recrystallisation.

The concentrating unit is operated such that the bottom product also contains small amounts of hydroquinone, in addition to the high-boiling concomitant substances. For example, the bottom product can contain 0.1 to 3% by weight of hydroquinone. The bottom product can in general be separated off in the form of a liquid. It is usually discarded.

The concentrating unit can be operated, for example, under a pressure of 30 to 200 mbars. It is preferably operated under a pressure of 35 to 150 mbars, and particularly preferably under 40 to 100 mbars.

The concentrating unit can also be operated by a procedure in which the bottom product from the second rectification column is allowed to solidify and is fed, in the solid form, to the concentrating unit and hydroquinone is separated off in this unit by sublimation. In this case, the pressure and temperature of the concentrating unit must be chosen such that evaporation of the solid phase is possible.

The evaporation operations necessary for carrying out the process steps according to the invention can in general be carried out in all evaporation apparatuses which are customary in industry. For example, circulatory evaporators or falling film evaporators are suitable. Thin film evaporators and screw evaporators are particularly suitable for the evaporation of hydroquinone which is to be carried out in the last step. Suitable columns which can be used in the process according to the invention are all the rectification columns customary in industry, for example packed columns or bubble tray columns. Perforated tray columns or columns with steel or ceramic packing are also very suitable.

All the industrial materials of construction which are stable in the temperature range from 0° to 250° C., towards the substances present are suitable for the apparatuses employed in the process according to the invention. Glass, titanium, enamelled steels or stainless steels with a high chromium and nickel content of, for example, in each case between 10 and 30% by weight are particularly suitable.

The temperatures at which the individual process steps are in general carried out are limited, on the one hand, by the boiling points, at the pressures indicated, of the particular substance(s) to be evaporated and, on the other hand, by the decomposition of the particular bottom product phase which can be observed at high temperatures. The decomposition of the bottom product phases starts at about 230° C. and is in general markedly pronounced from 250° C. The steps are thus in general carried out at temperatures below 230° C. They are preferably carried out at temperatures below 215° C., especially at locations where the residence times of the product are relatively long. In the case of short residence times, temperatures in the range from 230° to 250° C. can also be used.

The process according to the invention enables the products pyrocatechol and hydroquinone to be separated from one another and from phenol and high-boiling concomitant substances in a simpler manner than that used hitherto. Compared with the known processes for the isolation of pyrocatechol and hydroquinone, the process according to the invention requires considerably less energy, since pyrocatechol and hydroquinone are subjected to one less evaporation. A particular advantage of the process according to the invention is that the high-boiling substances must be isolated and separated off only at one point, that is to say as the bottom product of the concentrating unit. Another advantage of the process according to the invention is that gentle evaporation of the products pyrocatechol and hydroquinone is ensured. In all evaporators, that is to say at the points with the highest heat transfer, concomitant substances which transfer some of the heat and thus keep the exposure of the products to heat low are always present. The process according to the invention can be carried out under pressures which can be achieved by means which are customary in industry and are not particularly expensive.

It is regarded as decidedly surprising that sufficiently pure pyrocatechol and hydroquinone can be isolated in such a simple manner by the process according to the invention. Separating off of the high-boiling concomitant substances exclusively only at the end of the entire process was prejudiced on the basis of the processes known hitherto and of generally customary technological considerations. It was to be expected that these high-boiling concomitant substances form solids, deposits and/or blockages when passed through two rectification columns and a concentrating unit and thus, in particular, a continuous procedure for the entire process is associated with considerable problems. Surprisingly, however, the high-boiling concomitant substances remain in the liquid form in the bottom product phases in the process according to the invention and can thus be handled without particular problems.

EXAMPLE

A mixture of 51.1% by weight of phenol, 25.2% by weight of pyrocatechol, 17.7% by weight of hydroquinone and 5.9% by weight of high-boiling concomitant substances was fed continuously to a first glass rectification column which had an internal diameter of 50 mm, was packed with 4×4 mm glass rings and had a length of f1,200 mm in the rectifying section and 1,500 mm in the stripping section. The column was provided with adiabatic heating over sections of 500 mm in the rectifiying section and over sections of 750 mm in the stripping section, and with protective trace-heating over its entire length.

Phenol was obtained as the top product under an overhead pressure of 136 mbars and at a reflux ratio of 1 and a bottom temperature of 201° C.

The bottom product contained 52% by weight of pyrocatechol, 36% by weight of hydroquinone and 12% by weight of high-boiling concomitant substances.

The product mixture obtained as the bottom product from the first rectification column was fed continuously to a second glass rectification column with the following dimensions: diameter: 50 mm; packing: 4×4 mm glass rings rectifying section: 2,000 mm in length; stripping section; 1,000 mm in length.

The column was likewise provided with a protective trace-heating and, over the entire length, with an adiabatic heating jacket in sections of 42 mbars and at a ratio of reflux to removal of 2, pure pyrocatechol was taken off as the top product and a mixture of 75% by weight of hydroquinone and 25% by weight of concomitant substances was obtained at the bottom at 206° C.

The bottom product thus obtained was fed continuously to a thin film evaporator, in which hydroquinone was distilled off under 40 mbars and 186° C. and a liquid bottom product which contained 1% by weight of hydroquinone was obtained.

What is claimed is:

1. A process for the isolation of pyrocatechol and hydroquinone from mixtures which contain phenol, pyrocatechol, hydroquinone, and higher boiling substances which comprises:

(a) feeding said mixture to a first rectification column in which the phenol and any substances present which have a boiling point between those of the phenol and pyrocatechol are obtained as a top product, leaving behind a bottom product substantially free of phenol;

(b) feeding said bottom product from the first rectification column to a second rectification column, in which the pyrocatechol is obtained as top product leaving behind a bottom product containing hydroquinone and high boiling substances; and (c) feeding the bottom product from the second rectification, to a concentrating unit and therein evaporating hydroquinone overhead to leave behind high boiling substances as residue.

2. A process according to claim 1, wherein the mixture fed to the first rectification column is one obtained by reacting phenol with a peroxidic hydroxylating agent and removing from it the constituents with boiling points below that of phenol.

3. A process according to claim 2, wherein additionally from the reaction mixture some of the phenol employed in excess have been removed.

4. A process according to claim 1, wherein said mixture contains 10 to 85% by weight of phenol, 5 to 45% by weight each of pyrocatechol and hydroquinone and 0.5 to 10% by weight of high-boiling accompanying substances.

5. A process according to claim 1, wherein the rectification in the first rectification column is conducted under an over-pressure of from 5 to 700 mbars.

6. A process according to claim 1, wherein the first rectification column contains between 15 and 25 theoretical plates and is operated at a ratio of reflux to removal of 0.5 to 1.

7. A process according to claim 1, wherein the second rectification column is operated under an overhead pressure in the range from 0.02 to 0.2 bar.

8. A process according to claim 1, wherein the second rectification column contains between 12 and 16 theoretical plates and is operated at a ratio of reflux to removal of 1.8 to 2.5.

9. A process according to claim 1, wherein the concentration according to step "c" is effected under a pressure of 30 to 200 mbars.

10. A process according to claim 1, wherein the concentration according to step "c" is conducted such that the bottom product contains 0.1 to 3% by weight of hydroquinone.

11. A process according to claim 1, wherein the individual process steps are all carried out at temperatures below 230° C.

12. A process according to claim 1, wherein the mixture additionally contains substances which have boiling points between those of phenol and pyrocatechol.

13. A process for the isolation of pyrocatechol and hydroquinone from mixtures which contain phenol, pyrocatechol, hydroquinone, and higher boiling substances which consists essentially of:

(a) feeding said mixture to a first rectification column in which the phenol and any substances present which have a boiling point between those of the phenol and pyrocatechol are obtained as a top product, leaving behind a bottom product substantially free of phenol;

(b) feeding said bottom product substantially free of phenol and obtaind from the first rectification column to a second rectification column, in which the pyrocatechol is obtained as top product leaving behind a bottom product containing hydroquinone and high boiling substances; and (c) feeding the bottom product from the second rectification, to a concentrating unit and therein evaporating hydroquinone overhead to leave behind high boiling substances as residue.

* * * * *

UNITED STATES PATENT AND TRADEMARK OFFICE

CERTIFICATE OF CORRECTION

PATENT NO. : 4,308,112

DATED : December 29, 1981

INVENTOR(S) : Christoph Jupe; Jürgen Baumert; Günter Schümmer

It is certified that error appears in the above–identified patent and that said Letters Patent are hereby corrected as shown below:

Column 1, line 27, delete "(German Published"(first instance);
line 28, after "DE-OS (first instance) insert -- (German Published";
line 44, delete "Mimisci" and insert -- Minisci --.

Column 2, line 67, delete "pryocatechol" and insert -- pyro-catechol --.

Column 3, delete line 11;
line 30, delete "high" and insert -- higher --.

Column 6, line 14, delete "f1,200" and insert -- 1,200 --.
line 30, after "rings" insert a semi-colon (;);
line 31, after "section" change semi-colon(;) to a colon (:);
line 34, after "sections" insert -- each 500 mm long. Under an overhead pressure --.

Column 8, line 20, delete "obtaind" and insert -- obtained --.

Signed and Sealed this

*Twenty-seventh* Day of *April 1982*

[SEAL]

*Attest:*

GERALD J. MOSSINGHOFF

*Attesting Officer* *Commissioner of Patents and Trademarks*